(12) United States Patent
Funatsu et al.

(10) Patent No.: US 6,239,303 B1
(45) Date of Patent: May 29, 2001

(54) SILYLATION OF HYDROXYL GROUP-CONTAINING COMPOUND

(75) Inventors: Kenji Funatsu; Tohru Kubota; Mikio Endo, all of Nakakubiki-gun (JP)

(73) Assignee: Shin-Etsu Chemical Co., Ltd. (JP)

( * ) Notice: Subject to any disclaimer, the term of this patent is extended or adjusted under 35 U.S.C. 154(b) by 0 days.

(21) Appl. No.: 09/688,387

(22) Filed: Oct. 17, 2000

(30) Foreign Application Priority Data

Oct. 18, 1999 (JP) .................................................. 11-294899

(51) Int. Cl.⁷ ................................. C07F 7/08; C07F 7/18
(52) U.S. Cl. .............................................................. 556/470
(58) Field of Search ............................................. 556/470

(56) References Cited

U.S. PATENT DOCUMENTS 5,047,526 * 9/1991 Yamamoto ........................ 556/470 X

OTHER PUBLICATIONS

Bull. Chem. Soc. Jpn., 1989, 62, 2111.

Advances in Organometallic Chemistry, vol. 19, 1981, pp. 213–255, Academic Press.

J. Organomet. Chem., 1976, 114, 135.

J. Organomet. Chem., 1980, 192, 329.

Tetrahedon lett., 1992, 33, 5044.

* cited by examiner

Primary Examiner—Paul F. Shaver
(74) Attorney, Agent, or Firm—Millen, White, Zelano & Branigan, P.C.

(57) ABSTRACT

A hydroxyl group-containing compound is silylated by reacting it with an organohydrosilane compound in the presence of a ruthenium complex catalyst having carbonyl groups as ligands. Silylation takes place in a short time while the amount of the catalyst is minimized.

3 Claims, No Drawings

SILYLATION OF HYDROXYL GROUP-CONTAINING COMPOUND

This invention relates to a method for silylating a hydroxyl group-containing compound.

BACKGROUND OF THE INVENTION

For the silylation of hydroxyl groups, it is known in the art to silylate a hydroxyl group-containing compound with a hydrosilane compound as a silylating agent in the presence of a transition metal-carrying catalyst. The catalyst is generally in the form of active carbon or a similar carrier having metallic palladium, metallic rhodium or metallic ruthenium supported thereon. The method using such transition metal-carrying catalysts has several problems. First, the catalysts themselves are expensive. The post treatment of the transition metal-carrying catalysts is dangerous since hydrogen is occluded in the catalysts at the end of reaction. The catalysts are difficult to handle since they are heterogeneous catalysts using carriers. The method is thus disadvantageous for industrial synthesis. See Bull. Chem. Soc. Jpn., 1989, 62, 2111; and Advances in Organometallic Chemistry, Vol. 19, 1981, pp. 213–255, Academic Press. It is also known to use homogeneous catalysts in the form of various transition metal complexes such as rhodium, iridium and cobalt complexes. The method using these transition metal complexes also has the problem that the catalysts themselves are expensive. In addition, for reaction of a silylating agent having a sterically bulky substituent, these catalysts are low catalytic and must be used in large amounts. These catalysts are thus rather unacceptable on practical use. See J. Organomet. Chem., 1976, 114, 135; J. Organomet. Chem., 1980, 192, 329; and Tetrahedron Lett., 1992, 33, 5044.

SUMMARY OF THE INVENTION

An object of the invention is to provide a novel and improved method for silylating a hydroxyl group-containing compound with a hydrosilane compound in a short time using a minimized amount of a homogeneous catalyst.

It has been found that when a specific ruthenium complex, that is, a ruthenium complex having carbonyl groups as ligands is used as the catalyst, the hydroxyl group of a hydroxyl group-containing compound can be briefly silylated with a hydrosilane compound under substantially solventless conditions, and the amount of the catalyst used is minimized.

The invention provides a method for silylating a hydroxyl group-containing compound, comprising reacting a hydroxyl group-containing compound with an organohydrosilane compound in the presence of a ruthenium complex catalyst having carbonyl groups as ligands.

DESCRIPTION OF THE PREFERRED EMBODIMENT

The hydroxyl group-containing compounds to be silylated according to the invention include compounds having various functional groups such as alkyl alcohols, phenols and hydroxycarboxylic acids. Illustrative examples of the alkyl alcohol include primary alcohols such as methanol, ethanol, n-propyl alcohol, n-butyl alcohol, and n-hexyl alcohol, secondary alcohols such as isopropyl alcohol, sec-butyl alcohol and cyclohexyl alcohol, and tertiary alcohols such as tert-butyl alcohol and tert-amyl alcohol. Exemplary phenols include substituted or unsubstituted phenols such as phenol, 2-methylphenol, 3-methylphenol, and 4-methylphenol. Exemplary hydroxycarboxylic acids include hydroxybenzoic acid, hydroxyisobutyric acid, hydroxyvaleric acid and lactic acid.

The organohydrosilane compound used herein is not critical although it is preferably selected from compounds of the following general formulae (1) and (2).

$$R^1R^2R^3SiH \tag{1}$$

$$R^1R^2SiH_2 \tag{2}$$

Herein $R^1$, $R^2$ and $R^3$ may be the same or different, and stand for substituted or unsubstituted, monovalent hydrocarbon groups of 1 to 10 carbon atoms. Examples include straight or branched alkyl groups such as methyl, ethyl, propyl, isopropyl, butyl, isobutyl, tert-butyl, pentyl, hexyl and octyl; cycloalkyl groups such as cyclopentyl and cyclohexyl; aryl groups such as phenyl and tolyl; aralkyl groups such as benzyl, phenylethyl and phenylpropyl; and substituted ones of the foregoing groups in which some or all of the hydrogen atoms are replaced by halogen atoms (e.g., fluorine, chlorine and bromine atoms) or alkoxy groups of 1 to 8 carbon atoms (e.g., methoxy, ethoxy, propoxy, butoxy and hexyloxy).

Illustrative non-limiting examples of the hydrosilane compound include tri-substituted hydrosilanes such as trialkylhydrosilanes, dialkylarylhydrosilanes, alkyldiarylhydrosilanes, triarylhydrosilanes, trialkoxyhydrosilanes, dialkoxyalkylhydrosilanes, and alkoxydialkylhydrosilanes, and di-substituted hydrosilanes such as dialkyldihydrosilanes, diaryldihydrosilanes, and dialkoxydihydrosilanes. Of these, trimethylsilane, triethylsilane, triphenylsilane, tert-butyldimethylsilane, phenyldimethylsilane, trimethoxysilane and triethoxysilane are often used.

The silylating reaction catalyst used herein is a ruthenium organometallic complex. The ruthenium organometallic complex used herein should have carbonyl groups as ligands. The complex may have a halide (e.g., chloride or bromide ion), unsaturated hydrocarbon group or anion thereof, or saturated hydrocarbon group alone or in combination of two or more as another ligand. Illustrative examples of the ruthenium complex include dodecacarbonyl triruthenium, tetrachlorohexacarbonyl diruthenium, chlorodicarbonyl (cyclopentadienyl) ruthenium, bromotricarbonyl-(allyl) ruthenium, tricarbonyl (cyclooctatetraene) ruthenium, dicarbonylbis(allyl) ruthenium, tetracarbonyl-bis(cyclopentadienyl) diruthenium, and dicarbonyl(methyl)-(cyclopentadienyl) ruthenium.

It is noted that those ruthenium organometallic complexes having a phosphine ligand such as triphenylphosphine have a low catalytic activity and are undesirable.

The ruthenium complex is used in a catalytic amount, preferably in such an amount as to give about 0.001 to 1 mol %, and more preferably about 0.003 to 0.05 mol % of ruthenium atom based on the hydroxyl group-containing compound.

The method of the invention may be carried out either in a solvent or without a solvent. In the practice of the invention, reaction proceeds quickly in an essentially quantitative manner under solventless conditions. When a solvent is used, it may be selected from those solvents which are not sensitive to silylating reaction. Exemplary solvents are toluene, xylene, hexane, isooctane, cyclohexane, tetrahydrofuran, acetonitrile, and N-methyl-2-pyrrolidone.

In the practice of the invention, silylating reaction may be effected at any desired temperature. However, a temperature in the range of about 70 to 120° C. is appropriate when the catalyst stability and reaction rate are taken into account. The reaction time is generally about ½ to 10 hours.

Since hydrogen gas evolves upon reaction, the method of the invention is preferably carried out in an inert gas atmosphere such as nitrogen or argon.

The compounds resulting from the silylating method of the invention correspond to the starting hydroxyl group-containing compounds in which the hydrogen atom of a hydroxyl group is replaced by a $R^1R^2R^3Si$ group or $R^1R^2SiH$ group from the formula (1) or (2) or the like.

EXAMPLE

Examples of the invention are given below by way of illustration and not by way of limitation.

Example 1

A 100-ml four-necked flask equipped with a stirrer, reflux condenser, thermometer and dropping funnel was charged with 10.0 g (0.1 mol) of cyclohexanol and 2.1 mg (3.33× $10^{-3}$ mmol, 0.01 mol % Ru atom/cyclohexanol) of dodecacarbonyl triruthenium $Ru_3(CO)_{12}$. By heating at 80° C. and stirring, dodecacarbonyl triruthenium was dissolved. Thereafter, in a nitrogen atmosphere and at 80 to 90° C. 11.6 g (0.1 mol) of tert-butyldimethylsilane was added dropwise over 30 minutes from the dropping funnel. After the completion of dropwise addition of tert-butyldimethylsilane, the solution was ripened for 2 hours at 80 to 90° C. During ripening, the reaction solution was sampled at intervals of 1 hour and analyzed by gas chromatography whereby the percent conversion of cyclohexanol was tracked. After 2 hours of ripening, 96.0% of cyclohexanol had been converted to tert-butyldimethylcyclohexyloxysilane.

Example 2

A 100-ml four-necked flask equipped with a stirrer, reflux condenser, thermometer and dropping funnel was charged with 10.0 g (0.1 mol) of cyclohexanol and 2.6 mg (5.08× $10^{-3}$ mmol, 0.01 mol % Ru atom/cyclohexanol) of tetrachlorohexacarbonyl diruthenium $[RuCl_2(CO)_3]_2$. By heating at 80° C. and stirring, tetrachlorohexacarbonyl diruthenium was dissolved. Thereafter, in a nitrogen atmosphere and at 80 to 90° C., 11.6 g (0.1 mol) of tert-butyldimethylsilane was added dropwise over 30 minutes from the dropping funnel. After the completion of dropwise addition of tert-butyldimethylsilane, the solution was ripened for 2 hours at 80 to 90° C. During ripening, the reaction solution was sampled at intervals of 1 hour and analyzed by gas chromatography whereby the percent conversion of cyclohexanol was tracked. After 2 hours of ripening, 97.1% of cyclohexanol had been converted to tert-butyldimethylcyclohexyloxysilane.

Comparative Example 1

A 100-ml four-necked flask equipped with a stirrer, reflux condenser, thermometer and dropping funnel was charged with 10.0 g (0.1 mol) of cyclohexanol and 0.46 g (0.5 mmol, 0.5 mol %/cyclohexanol) of chlorotristriphenyl-phosphine rhodium $RhCl(PPh_3)_3$. In a nitrogen atmosphere and at 80 to 90° C., 11.6 g (0.1 mol) of tert-butyldimethylsilane was added dropwise over 30 minutes from the dropping funnel. After the completion of dropwise addition of tert-butyldimethylsilane, the solution was ripened for 6 hours at 80 to 90° C. During ripening, the reaction solution was sampled at intervals of 2 hours and analyzed by gas chromatography whereby the percent conversion of cyclohexanol was tracked. After 6 hours of ripening, the conversion of cyclohexanol to tert-butyldimethylcyclo-hexyloxysilane was 0%.

Comparative Example 2

A 100-ml four-necked flask equipped with a stirrer, reflux condenser, thermometer and dropping funnel was charged with 10.0 g (0.1 mol) of cyclohexanol and 0.39 g (0.5 mmol, 0.5 mol %/cyclohexanol) of chlorocarbonyl-bistriphenylphosphine iridium $IrCl(CO)(PPh_3)_2$. In a nitrogen atmosphere and at 80 to 90° C., 11.6 g (0.1 mol) of tert-butyldimethylsilanewas added dropwise over 30 minutes from the dropping funnel. After the completion of dropwise addition of tert-butyldimethylsilane, the solution was ripened for 6 hours at 80 to 90° C. During ripening, the reaction solution was sampled at intervals of 2 hours and analyzed by gas chromatography whereby the percent conversion of cyclohexanol was tracked. After 6 hours of ripening, the conversion of cyclohexanol to tert-butyldimethylcyclohexyloxysilane was 0%.

Comparative Example 3

A 100-ml four-necked flask equipped with a stirrer, reflux condenser, thermometer and dropping funnel was charged with 10.0 g (0.1 mol) of cyclohexanol and 0.48 g (0.5 mmol, 0.5 mol %/cyclohexanol) of dichlorotristriphenyl-phosphine ruthenium $RuCl_2(PPh_3)_3$. In a nitrogen atmosphere and at 90° C., 11.6 g (0.1 mol) of tert-butyldimethylsilane was added dropwise over 30 minutes from the dropping funnel. After the completion of dropwise addition of tert-butyldimethylsilane, the solution was ripened for 8 hours at 80 to 90° C. During ripening, the reaction solution was sampled at intervals of 2 hours and analyzed by gas chromatography whereby the percent conversion of cyclohexanol was tracked. After 8 hours of ripening, the conversion of cyclohexanol to tert-butyldimethylcyclohexyl-oxysilane was 3.1%.

Comparative Example 4

A 100-ml four-necked flask equipped with a stirrer, reflux condenser, thermometer and dropping funnel was charged with 10.0 g (0.1 mol) of cyclohexanol and 1.065 g (0.5 mmol, 0.5 mol %/cyclohexanol) of 5% palladium on carbon Pd/C. In a nitrogen atmosphere and at 80 to 90° C., 11.6 g (0.1 mol) of tert-butyldimethylsilane was added dropwise over 30 minutes from the dropping funnel. After the completion of dropwise addition of tert-butyldimethylsilane, the solution was ripened for 6 hours at 80 to 90° C. During ripening, the reaction solution was sampled at intervals of 2 hours and analyzed by gas chromatography whereby the percent conversion of cyclohexanol was tracked. After 6 hours of ripening, the conversion of cyclohexanol to tert-butyldimethylcyclohexyloxysilane was 2.9%.

Examples 3–24

Using the hydroxyl group-containing compound and organohydrosilane compound shown in Table 1, reaction was effected in a nitrogen atmosphere under the reaction conditions (including the catalyst, catalyst amount, reaction temperature and reaction time) shown in Table 1. Each reaction solution was analyzed by gas chromatography, from which a percent conversion was calculated on the alcohol basis.

TABLE 1

| Example | Hydroxyl group-containing compound | Organo-hydrosilane compound[1] | Time (hr) | Temperature (° C.) | Catalyst amount (mol %)[2] | Catalyst | Conversion (%) |
|---|---|---|---|---|---|---|---|
| 3 | cyclohexanol | HBS | 3 | 80~90 | 0.003 | $Ru_3(CO)_{12}$ | 95.6 |
| 4 | cyclohexanol | HBS | 2 | 80~90 | 0.03 | $Ru_3(CO)_{12}$ | 96.8 |
| 5 | cyclohexanol | HBS | 1 | 80~90 | 0.1 | $Ru_3(CO)_{12}$ | 96.9 |
| 6 | cyclohexanol | HBS | 1 | 80~90 | 0.03 | $[RuCl_2(CO)_3]_2$ | 97.8 |
| 7 | 1-propanol | HBS | 0.5 | 80~90 | 0.01 | $Ru_3(CO)_{12}$ | 99.4 |
| 8 | 1-butanol | HBS | 0.5 | 80~90 | 0.01 | $Ru_3(CO)_{12}$ | 96.9 |
| 9 | 1-butanol | HBS | 0.5 | 80~90 | 0.01 | $[RuCl_2(CO)_3]_2$ | 97.8 |
| 10 | 1-hexanol | HBS | 1 | 80~90 | 0.01 | $Ru_3(CO)_{12}$ | 98.7 |
| 11 | 1-octanol | HBS | 10 | 80~90 | 0.01 | $Ru_3(CO)_{12}$ | 89.8 |
| 12 | 2-propanol | HBS | 2 | 80~90 | 0.01 | $Ru_3(CO)_{12}$ | 98.6 |
| 13 | 2-butanol | HBS | 3 | 80~90 | 0.01 | $Ru_3(CO)_{12}$ | 98.8 |
| 14 | 2-butanol | HBS | 3 | 80~90 | 0.01 | $[RuCl_2(CO)_3]_2$ | 98.5 |
| 15 | 3-pentanol | HBS | 3 | 80~90 | 0.01 | $Ru_3(CO)_{12}$ | 94.6 |
| 16 | cyclopentanol | HBS | 3 | 80~90 | 0.01 | $Ru_3(CO)_{12}$ | 97.3 |
| 17 | 1-propanol | TES | 0.5 | 80~90 | 0.01 | $Ru_3(CO)_{12}$ | 99.9 |
| 18 | 1-butanol | TES | 0.5 | 80~90 | 0.01 | $Ru_3(CO)_{12}$ | 99.8 |
| 19 | 2-butanol | TES | 0.5 | 80~90 | 0.01 | $Ru_3(CO)_{12}$ | 99.9 |
| 20 | cyclopentanol | TES | 0.5 | 80~90 | 0.01 | $Ru_3(CO)_{12}$ | 99.8 |
| 21 | t-amyl alcohol | TES | 1 | 110~120 | 0.03 | $Ru_3(CO)_{12}$ | 98.1 |
| 22 | 1-methylcyclohexanol | TES | 1 | 110~120 | 0.03 | $Ru_3(CO)_{12}$ | 97.7 |
| 23 | 2-butanol | TES | 0.5 | 80~90 | 0.01 | $[RuCl_2(CO)_3]_2$ | 99.3 |
| 24 | t-amyl alcohol | TES | 1 | 110~120 | 0.03 | $[RuCl_2(CO)_3]_2$ | 98.5 |

Note:
[1])HBS: tert-butyldimethylhydrosilane
TES: triethylhydrosilane
[2])The catalyst amount is expressed in mol % of Ru atom based on the alcohol while an equivalent of the hydrosilane was used per alcohol.

According to the invention, a hydroxyl group-containing compound can be silylated in a short time while the amount of the catalyst is minimized.

Japanese Patent Application No. 11-294899 is incorporated herein by reference.

Reasonable modifications and variations are possible from the foregoing disclosure without departing from either the spirit or scope of the present invention as defined by the claims.

What is claimed is:

1. A method for silylating a hydroxyl group-containing compound, comprising reacting a hydroxyl group-containing compound with an organohydrosilane compound in the presence of a ruthenium complex catalyst having carbonyl groups as ligands.

2. The silylating method of claim 1 wherein the organohydrosilane compound has the following general formula (1) or (2):

$$R^1R^2R^3SiH \qquad (1)$$

$$R^1R^2SiH_2 \qquad (2)$$

wherein $R^1$, $R^2$ and $R^3$ are independently selected from substituted or unsubstituted, monovalent hydrocarbon groups of 1 to 10 carbon atoms.

3. The silylating method of claim 2 wherein the organohydrosilane compound is tert-butyldimethylhydrosilane.

* * * * *